United States Patent
Heikkilä et al.

(10) Patent No.: US 11,657,904 B2
(45) Date of Patent: May 23, 2023

(54) METHOD AND APPARATUS FOR ADJUSTING EVENT TIMESTAMP RELATING TO CLINICAL TRIAL

(71) Applicant: SIGNANT HEALTH GLOBAL LLC, Blue Bell, PA (US)

(72) Inventors: Arttu Heikkilä, Vantaa (FI); Mika Jalkanen, Espoo (FI); Mika Lankinen, Lepsämä (FI)

(73) Assignee: CRF BOX OY, Helsinki (FI)

( * ) Notice: Subject to any disclaimer, the term of this patent is extended or adjusted under 35 U.S.C. 154(b) by 1080 days.

(21) Appl. No.: 15/627,639

(22) Filed: Jun. 20, 2017

(65) Prior Publication Data
US 2018/0004916 A1  Jan. 4, 2018

(30) Foreign Application Priority Data
Jun. 29, 2016 (GB) .................................... 1611256

(51) Int. Cl.
| | | |
|---|---|---|
| G16H 10/20 | (2018.01) | |
| G06F 16/23 | (2019.01) | |
| G16H 10/65 | (2018.01) | |
| G16H 40/67 | (2018.01) | |

(52) U.S. Cl.
CPC ......... *G16H 10/20* (2018.01); *G06F 16/2358* (2019.01); *G16H 10/65* (2018.01); *G16H 40/67* (2018.01)

(58) Field of Classification Search
CPC .............................. G16H 10/60; A61B 5/4836
See application file for complete search history.

(56) References Cited

U.S. PATENT DOCUMENTS

| | | | |
|---|---|---|---|
| 8,719,452 B1 | 5/2014 | Ding et al. | |
| 2010/0169114 A1* | 7/2010 | Henderson | G16H 70/00 707/769 |
| 2013/0275151 A1* | 10/2013 | Moore | G16H 40/63 705/3 |
| 2015/0207886 A1 | 7/2015 | Callaghan et al. | |
| 2015/0302179 A1* | 10/2015 | Rheault | G16Z 99/00 705/2 |
| 2016/0098537 A1* | 4/2016 | Dettinger | G16H 40/63 600/509 |
| 2016/0110523 A1* | 4/2016 | Francois | G16H 10/20 705/2 |

OTHER PUBLICATIONS

Extended European Search Report received for European Patent Application No. EP17177040.7, dated Aug. 23, 2017, 11 pages.

* cited by examiner

*Primary Examiner* — Reginald R Reyes
(74) *Attorney, Agent, or Firm* — Hogan Lovells US LLP

(57) ABSTRACT

A computer implemented method includes receiving an event log corresponding to event entries of an electronic diary of a participant of a clinical trial, wherein the event log is generated in a client device, and the event log includes an event identifier and an event timestamp for at least two event entries; determining a block of event entries within the event log, the block including a first event entry and a second event entry at least one of whose event timestamps are verified being correct in view of corresponding service timestamps of a server apparatus, wherein the first and the second event entry are arranged chronologically; and adjusting the event timestamp of the second event entry based on the first timestamp.

16 Claims, 4 Drawing Sheets

METHOD AND APPARATUS FOR ADJUSTING EVENT TIMESTAMP RELATING TO CLINICAL TRIAL

TECHNICAL FIELD

The present application generally relates to clinical trials and adjusting timestamps of electronic diary related events reported by a participant of the clinical trial.

BACKGROUND

This section illustrates useful background information without admission of any technique described herein representative of the state of the art.

New medical innovations, such as new drugs or medical devices, are often researched and tested using clinical trials. Trials require more than one phase of testing that take several years and cost considerable amounts of money to perform.

Clinical trials are typically classified into 4 phases (unless trial is interrupted or closed). Clinical trials of drugs may not fit into a single phase. For example, some clinical trials may blend from phase I to phase II or from phase II to phase III. The drug-development process may normally proceed through all four phases over many years. If a drug successfully passes through phases I, II and III, the drug may be approved by the national regulatory authority for use in general population, for example. Phase IV may correspond to 'post-approval' studies.

Each phase has a different purpose and helps researchers answer different questions. In phase I trials, researchers test an experimental drug or treatment in a small group of people (20-80) for the first time. The purpose is to evaluate its safety and identify side effects. In phase II trials, the experimental drug or treatment is administered to a larger group of people (100-300) to determine its effectiveness and to further evaluate its safety. In phase III trials, the experimental drug or treatment is administered to large groups of people (1,000-3,000) to confirm its effectiveness, monitor side effects, compare it with standard or equivalent treatments, and collect information that will allow the experimental drug or treatment to be used safely. In phase IV trials, after a drug is approved by a regulatory authority, such as Food and Drug Administration (FDA) in the USA, and made available to the public, researchers track its safety, seeking more information about a drug or treatment's risks, benefits, and optimal use.

One reason for the length and cost of clinical trials is the need to independently review and submit data and documentation for a clinical trial. The review and submission cannot traditionally be performed until all information is collected, documented, validated and analysed.

Typically, a clinical trial or study is funded by a sponsor, such as a private company, medical or research institution, federal agency, or by an entity established by a collaboration of such groups. The sponsor may employ one or more clinical investigators or research assistants to oversee administration of and/or monitor the study at one or more investigation sites. Each investigation site may include a number of study participants.

When a participant in a clinical trial fills in the electronic diary, time and date when a record or a set of records have been filled in need to be known by the receiving party. There are problems associated with a correctness of the time and date at which the participant entered the data to the electronic diary, since there are many reasons that may cause the client device to be set to a wrong date and time, with regards to a clinical trial.

Thus, a service solution is needed to enable more accurate and efficient collecting, reviewing, and correcting clinical trial related data. More particularly, there is a need for systems and methods for automatically processing the complex and vast clinical trial data and adjusting timestamps of the clinical trial data.

SUMMARY

Various aspects of examples of the invention are set out in the claims.

According to a first example aspect of the present invention, there is provided a computer implemented method comprising:

receiving an event log corresponding to event entries of an electronic diary of a participant of a clinical trial, wherein the event log is generated in a client device, and the event log comprising at least two event entries, each of the at least two event entries associated with an event identifier and an event timestamp;

determining a block of event entries within the event log, the block comprising a first event entry and a second event entry at least one of whose event timestamps are verified being correct in view of corresponding service timestamps of a server apparatus, wherein the first and the second event entry are arranged chronologically; and adjusting the event timestamp of at least one of the first and the second event entry based on the timestamp verified being correct.

In an embodiment, a computer implemented method comprises:

receiving an event log corresponding to event entries of an electronic diary of a participant of a clinical trial, wherein the event log is generated in a client device, and the event log comprising an event identifier and an event timestamp for at least two event entries;

determining a block of event entries within the event log, the block comprising a first event entry and a second event entry at least one of whose event timestamps are verified being correct in view of corresponding service timestamps of a server apparatus, wherein the first and the second event entry are arranged chronologically; and adjusting the event timestamp of the second event entry based on the event timestamp of the first event entry.

In an embodiment, the method further comprises:

receiving the event log corresponding to event entries of an electronic diary of a participant of a clinical trial, wherein the event log is generated in a client device, and the event log comprising an event identifier and an event timestamp for at least three event entries;

determining a block of event entries within the event log, the block comprising a first event entry and a second event entry at least one of whose event timestamps are verified being correct in view of corresponding service timestamps of a server apparatus, wherein the second event entry having a later event timestamp than the first event entry;

detecting a third event entry whose event timestamp is temporally between the first and second timestamps; and adjusting the event timestamp of the third event entry based on at least one of the first and the second timestamps.

In an embodiment, the method further comprises:

generating a tag to at least one event entry for indicating the adjusting of the event timestamp.

In an embodiment, the method further comprises:
receiving the event log from the client device; and
maintaining the event log generated by the electronic diary at the server apparatus for clinical trial processing.

In an embodiment, the method further comprises:
receiving participant data from the client device or a personal device; and
maintaining the event log and the participant data generated by the electronic diary at the server apparatus for clinical trial processing.

In an embodiment, the personal device comprises a user wearable device.

In an embodiment, the participant data is recorded by the personal device without user input.

In an embodiment, the participant data is recorded by the electronic diary before sending to the server apparatus.

In an embodiment, the method further comprises:
maintaining a local clock information at the client device for providing event timestamps for the event entries; and
maintaining trusted clock information at the server apparatus for providing service timestamps used for verification of event timestamps of event entries.

In an embodiment, at least one of the electronic diary and the event log is associated with a participant identifier or a client device identifier of the participant of the clinical trial.

In an embodiment, the method further comprises:
determining a time correction for the event timestamp of the second event; and
adjusting the event timestamp of the second event entry based on the time correction; and
adjusting the event timestamp of the third event entry based on the time correction.

In an embodiment, the method further comprises:
determining a minimum time value for the event timestamp of the third event based on the event timestamp of the of the third event and a timestamp of at least one previous event;
determining a maximum time value for the event timestamp of the third event based on the event timestamp of the of the third event and a timestamp of at least one following event;
defining a time range using the minimum time value and the maximum time value; and
adjusting the event timestamp of the third event entry based on the time range.

In an embodiment, the method further comprises:
approving the event entry as valid entry for trial data of the clinical trial in response to generation of the tag indicating automatic adjusting of the event timestamp.

In an embodiment, the method further comprises:
synchronizing the local clock of the client device using the trusted clock of the server apparatus.

In an embodiment, the synchronization is done when the client device and the server apparatus are connected to each other for data transfer.

In an embodiment, the method further comprises retrieving the trial data of the on-going clinical trial from trial records maintained at the server apparatus.

In an embodiment, retrieving the trial data includes retrieving the trial data having a level of cleanliness satisfying a predetermined criterion of cleanliness.

In an embodiment, the predetermined criterion of a cleanliness comprises at least one of the following:
threshold value for an amount of event entries comprising a tag for indicating automatic adjusting of the event timestamp; and
threshold value for a proportional share of event entries comprising a tag for indicating automatic adjusting of the event timestamp.

In an embodiment, the method further comprises:
generating a synchronization message for a client device in response to adjusting the event timestamp of the third event entry, wherein the synchronization message comprising time correction value; and
transmitting the synchronization message for the client device for synchronizing a local clock of the client device based on the time correction value.

According to a second example aspect of the present invention, there is provided a server apparatus comprising:
a communication interface for transceiving information over a network;
at least one memory including computer program code;
the at least one memory and the computer program code configured to, with the at least one processor, cause the server apparatus to:
receive an event log corresponding to event entries of an electronic diary of a participant of a clinical trial, wherein the event log is generated in a client device, and the event log comprising at least two event entries, each of the at least two event entries associated with an event identifier and an event timestamp;
determine a block of event entries within the event log, the block comprising a first event entry and a second event entry at least one of whose event timestamps are verified being correct in view of corresponding service timestamps of a server apparatus, wherein the first and the second event entry are arranged chronologically; and
adjust the event timestamp of at least one of the first and the second event entry based on the timestamp verified being correct.

In an embodiment, the server apparatus is configured to:
receive an event log corresponding to event entries of an electronic diary of a participant of a clinical trial, wherein the event log is generated in a client device, and the event log comprising an event identifier and an event timestamp for at least two event entries;
determine a block of event entries within the event log, the block comprising a first event entry and a second event entry at least one of whose event timestamps are verified being correct in view of corresponding service timestamps of a server apparatus, wherein the first and the second event entry are arranged chronologically; and
adjust the event timestamp of the second event entry based on the event timestamp of the first event entry.

According to a third example aspect of the present invention, there is provided a computer program embodied on a computer readable non-transitory medium comprising computer executable program code, which when executed by at least one processor of an apparatus, causes the apparatus to:
receive an event log corresponding to event entries of an electronic diary of a participant of a clinical trial, wherein the event log is generated in a client device, and the event log comprising at least two event entries, each of the at least two event entries associated with an event identifier and an event timestamp;
determine a block of event entries within the event log, the block comprising a first event entry and a second event entry at least one of whose event timestamps are verified being correct in view of corresponding service timestamps of a server apparatus, wherein the first and the second event entry are arranged chronologically; and adjust the event timestamp of at least one of the first and the second event entry based on the timestamp verified being correct.

In an embodiment, the computer executable program code is configured to:

receive an event log corresponding to event entries of an electronic diary of a participant of a clinical trial, wherein the event log is generated in a client device, and the event log comprising an event identifier and an event timestamp for at least two event entries;

determine a block of event entries within the event log, the block comprising a first event entry and a second event entry at least one of whose event timestamps are verified being correct in view of corresponding service timestamps of a server apparatus, wherein the first and the second event entry are arranged chronologically; and adjust the event timestamp of the second event entry based on the event timestamp of the first event entry.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Figure 1:
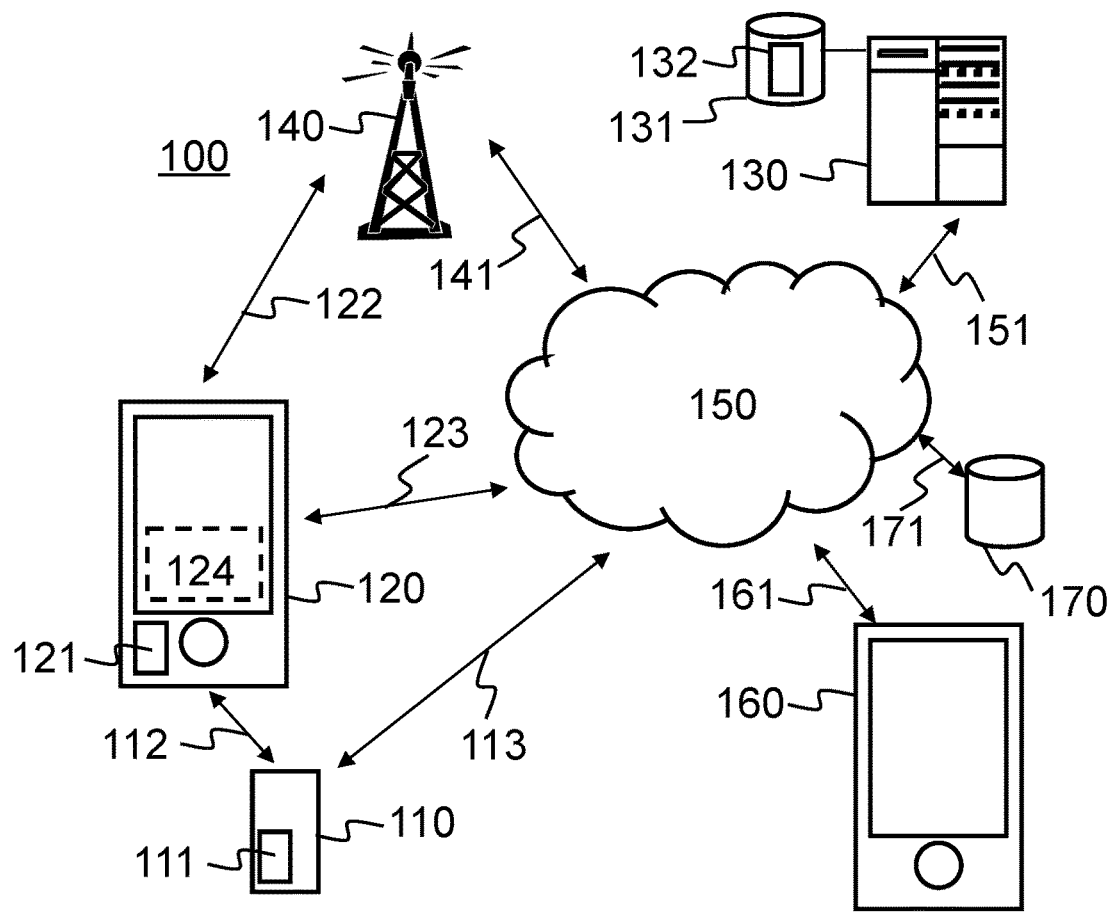
FIG. 1 shows a schematic drawing of a system of an example embodiment.

An example embodiment of the present invention and its potential advantages are understood by referring to FIGS. 1 through 6 of the drawings. In this document, like reference signs denote like parts or steps.

An electronic diary is a tool used during a clinical trial to register assessment of a participant's condition (e.g. symptom severity, quality of life) by the participant. The electronic diary registers data in a storage device and allows for automatically monitoring the time the entry was made. Frequent recording of symptoms using a diary helps to reduce recall bias. Electronic diaries enable entries are made as scheduled, and not, for example, in a batch immediately before the clinic visit. Electronic diaries also enable finding out if a participant takes the medication according to the treatment schedule, which is important during clinical trials. Investigators, on the other hand, are assessing the received data that was registered by the electronic diary.

In an embodiment, an electronic diary 124 may comprise a computer-implemented client software application for a participant of a clinical trial to record data for the clinical trial. The electronic diary 124 may also comprise a computer-implemented web browser application. The electronic diary 124 may also comprise a combination of a client software application and a browser application.

The electronic diary 124 allow only registered participant to record data. Typically, the electronic diary 124 may remind the participant to fill in data at the right time and may present only questions the participant should answer at that time, for example. In addition, the electronic diary 124 may time stamp the recorded data and maintain an audit trail of changes to the data in order to ensure the integrity and validity of the clinical trial related data.

The use of electronic diaries is regulated by laws and guidelines from local authorities as well as GCP (Good Clinical Practice). These regulations typically require that participants/patients are authenticated prior to entering the electronic diary to ensure that patient privacy is not compromised and to ensure that the data is recorded by the participant/patient and not by someone else.

In an embodiment, the electronic diary 124 may require login identification information to participants allowed to use the electronic diary 124. The identification information may comprise a participant login name and an associated password. The term "participant" refers to a person (such as e.g. a patient, a guardian of the patient, a care giver of the patient, or an observer of the patient or an animal, for example) using an electronic diary to record and submit participant-reported data (such as participant diary data or other related clinical data, for example) for use in clinical trials run by pharmaceutical industry, for example. Typically, the participant needs to be registered before allowed in the clinical trial. The participant utilizes an electronic diary 124 within a client device 120 (such as a smart phone, a personal digital assistant, a tablet or a laptop computer, for example) to record and send participant data.

In an embodiment, a client device 120 may be used by a plurality of participants. In such case the client device 120 may generate event entries of different participants to be transmitted to the server 130, 131 using the same client device identifier. Thus, the event entries from a single client device 120 but from different participants may be used for determining a block of event entries within the event log, wherein the block comprising a first event entry and a second event entry at least one of whose event timestamps are verified being correct in view of corresponding service timestamps of a server apparatus, wherein the first and the second event entry are arranged chronologically; and adjusting the event timestamp of the second event entry based on the first timestamp Then, participant data and an identifier of the participant are received at a participant data collector server 130, 131. The participant data is entered by the participant using the client device 120 or a personal device 110 without user input. Thus, the participant data is recorded by the electronic diary 124 that sends the participant data to the data collector server 130, 131. The personal device 110, such as a wearable device, may independently send data to the server 130, 131 or to the electronic diary 124, to be appended to the participant data. In case the personal device 110 sends independently the data to the server 130, 131, the personal device may transmit an event log corresponding to event entries of an electronic diary of a participant of a clinical trial, wherein the event log is generated in the personal device, and the event log comprising an event identifier and an event timestamp for at least one event entry that can be associated to participant data for investigation at the server 130, 131 based on a device identifier or participant identifier, for example.

A typical clinical trial begins with the construction of a clinical protocol that describes how a trial is to be performed, what data elements are to be collected, and what medical conditions need to be reported immediately to the pharmaceutical sponsor and the regulatory authority, such as Food and Drug Administration (FDA) in the USA, for example. The clinical protocol and its author are the ultimate authority on the conduct of the clinical trial. This protocol is the basis for every action performed by multiple players in diverse locations during the entire conduct of the trial. Any deviations from the protocol specifications, no matter how well intentioned, threaten the viability of the data and its usefulness for the regulatory authority, such as Food and Drug Administration (FDA) submission in the USA, for example.

Participant compliance is important for a clinical trial. Participant may be required to take medication and follow the regimen at times specified by the protocol. Additionally, an electronic diary is filled to provide participant data at times specified by the protocol. For instance, the protocol may specify that the participant needs to take certain drug at certain times. The protocol may define, for example, that certain drug should be taken on Day1 and report symptoms on Day2 and again on Day3, Day4, Day5, etc., each entry with their own date/timestamp.

Time stamp correctness of event entries may not be limited to one instance only but the protocol may be complicated: one event entry is filled in at time1, stored locally, other event entry is filled at time2, stored locally, other event entry is filled at time3, and then all event entries are collected and forwarded to send queue within the client device 120 to be sent when the device 120 is connected to network 150 and the transmission of participant data is triggered.

Many reasons may cause a client device 120 to be set to a wrong date and time, with regards to a clinical trial. For instance time zone changes may be causing problems, either occurring automatically, or due to actions by the user/participant. When the trial participant is traveling near a border of two countries, like the long E8 road in Lapland next to the border of Finland and Sweden border, with the client device 120 set to select network automatically, the device 120 may automatically connect to the strongest network signal available, including all the networks of the roaming partners of the home network operator. All that, combined with the device's 120 ability to local time and date provisioning, such as NITZ (Network Identity and Time Zone) may set time wrong and sometimes result as too early timestamps to an entered patient data record. NITZ is a mechanism for provisioning local time and date, time zone and DST offset, as well as network provider identity information, to mobile devices via a wireless network.

Another example where time may be set wrong is when the participant fills in the form while in a car in home soil and connected to home network, and when the participant a moment later sends the form data, the device 120 may be connected to the operator's roaming partner network, with a current time obtained from that roaming partner network even though the participant physically is still in home soil. The whole record may get a timestamp at the time of sending of the data. Then again, if timestamps are acquired and stored when the participant took the medicine or filled in a diary entry, the times may be totally different.

Participants may also travel across the time zones. Some devices 120 automatically change the date and time while some do not. This should be recognized by the server 130, 131.

Daylight savings (DST) in different countries at different times may also cause problems when the user travels to a country from a country where the trial takes place. As some countries where DST is in use start or end DST in different times, this may increase possibilities of wrong time stamps.

User of the client device 120 may change time/date manually and incorrectly that causes unreliable timestamps for the entry events of the electronic diary.

Sometimes, in case time is obtained from the network 140, 150, there might be some inaccuracies with real time clocks that might cause some problems with the current time.

It is possible that device 120 battery is drained, causing a full time/date reset. Some devices remember the last time when the device was switched on or used. Some devices also have a backup battery to preserve the time if the main battery runs dry, but during long storage these may run out too.

Odd firmware behaviour may also affect the timestamp.

Clinical trials typically last years. For a given trial, or for long-term clinical trial use, a sponsor may make an investment decision to lease or purchase a large amount of devices for trial use, which is a considerable investment. Typically these devices will not be upgraded to newer models every two years but they're used until they reach the end of their lifecycle or when the trial is over. During storage time their batteries may run out of power and depending on the make and model of the devices (or firmware version), their clocks will be reset to a default time, typically to a day in the year of manufacturing of the device, like 1.1.2001.

When a device 110, 120 is taken into use in a trial, perhaps after a long storage time, it's not guaranteed that the time will be set to a correct time. For instance the study coordinator may forget, or ignore to set a correct time despite instructions provided, the device 110, 120 may not have any kind of connection to any network 140, 150 in order to get a correct time from a network element or a service provider.

All the reasons above may lead into a situation where initially there's no clue as to at what time the device was taken into use in a trial, as the time stamps in the electronic diary records may be the default 1.1.2001 or anything between that and current time, or even a totally off this world time (accidentally) set by the user—and until the participant, or any other party using or monitoring the use of the device or the trial management software notices that the time and/or date of the device is wrong, the records entered by the participant may contain a wrong date and time stamp, for instance the default reset time 1.1.2001 at 0:00 am.

Should there always be a network connection available for a device, some of these problems would be rather easily overcome, but the nature of electronic diary means that the electronic diary should be designed for offline use. It is actually preferable to disable any network connections during filling of the electronic diary for several reasons to avoid distractions, such as incoming communication, so as to provide as close an experience to a pen-and-paper experience as possible to a participant.

As discussed above, the participants of the clinical trial cannot be prohibited to live normal life. If they want to go fishing or hiking, out of network coverage, they must be allowed to do so. A clinical trial protocol must not govern their personal life.

Another reason for preferring a disconnected mode for an electronic patient diary: some participants may have a data plan and they choose to set mobile data off from time to time or when they receive a notification that their data quota is about to reach the limit. They may get connected again when they're within a reach of a Wi-Fi access point or when they purchase more quota or when they start another month on their data plan. BYOD "Bring Your Own Device" may be used by the participants and BYOD device means allowing participants in a clinical trial to use their own computer devices to access and respond to study related questionnaires. BYOD device may comprise, for example, a smart phone, a laptop, a desktop PC, a user wearable smart device or an Internet enabled TV.

Further, some people have assumed full "Wi-Fi-only" profile, so they only get online when connected to a Wi-Fi network.

Again, during those non-connected times the internal clock of the device 120 may have missed a beat or may have been reset to a default time, causing newly entered diary records to contain wrong timestamps, unless the time is manually set, corrected or obtained automatically.

FIG. 1 shows a schematic picture of a system 100 according to an example embodiment of the invention.

The system comprises a client device 120 that may comprise a multimedia device, a mobile phone, an Internet tablet or a laptop computer, for example. The client device 120 is capable of downloading and locally executing software program code. The software program code may be a client application of a service whose server application is running on the server apparatus 130 of the system 100. The client device 120 may comprise a metadata element 121 for creating data usable as metadata relating to event entries of an electronic diary of a participant participating a clinical trial, wherein the electronic diary and the event log are generated in the client device 120.

The metadata element 121 may comprise at least one of the following: a microphone, a positioning device for determining the current location of the participant apparatus 120, and a local clock. The client device 120 is configured to be connectable to a wireless communication network 140 over a wireless connection 122. The wireless connection 122 may comprise a mobile cellular network or a wireless local area network (WLAN), for example. The wireless communication network 140 may be connected to a public data communication network 150, for example to the Internet, over a data connection 141. The client application may be operable also in offline mode and there is no need to have online connection over the network to the server 130, 131 all the time. In offline mode, the client device 120 may store application related data to cache memory and update the data to the server 130, 131 once getting the online access.

In an embodiment, the system 100 comprises a personal device 110 configured to be capable of capturing clinical trial related data. The personal device 110 may comprise a storage 111 for the trial related data. The storage 111 may comprise a flash memory card, for example. The personal device 110 is configured to be connectable to the client device 120 over a data connection 112. The data connection 112 may be a wired connection or a wireless connection. The wired connection may comprise Universal Serial Bus (USB), High-Definition Multimedia Interface (HDMI) or local area network (LAN), for example. The wireless connection may comprise Bluetooth™, Radio Frequency Identification (RF-ID) or wireless local area network (WLAN), for example.

The personal device 110 is configured to send captured data over the data connection 112 to the client device 120. Such transmittal may be initiated by a participant of the personal device 110, by a participant of the client device 120, or automatically based on settings. Such settings may comprise for example time of the day, amount of newly captured clinical trial related data or existence of the data connection 112 for the personal device 110.

In an embodiment, a participant of a clinical trial, may utilise a client device 120 for generating and transmitting clinical trial related data to a server apparatus 130, 131. Additionally a personal device 110 may be used but not necessarily. An event log corresponding to event entries of an electronic diary of a participant of a clinical trial is generated, wherein the event log is generated in a client device 120 (together or without the personal device 110), and the event log comprising an event identifier and an event timestamp for an event entry.

A block of event entries within the event log is determined at the server apparatus 130, 131, the block comprising a first event entry and a second event entry at least one of whose event timestamps are verified being correct in view of corresponding service timestamps of a server apparatus, wherein the second event entry having a later event timestamp than the first event entry. A third event entry is detected whose event timestamp is temporally between the first and second timestamps, and the event timestamp of the third event entry is adjusted based on at least one of the first and the second timestamps; and a tag is generated to the third event entry for indicating the adjusting of the event timestamp.

The clinical trial related data may be sent from the client device 120 to the system server 130. At the system server 130, the received data may be analysed and corrected.

The participant may be a human or an animal. In case of the animal, an owner of the animal may operate the client device 120 and provide necessary interaction with the system 100 or the animal may be wearing a personal device 110, for example.

In an embodiment, the system 100 comprises a server apparatus 130, which comprises a storage device 131 for storing clinical trial related information, such as electronic diary data, event logs and metadata received over a data connection 151, profile information of participants, history information of participants, clinical trial information, client software application data and server software application data, for example.

In an embodiment, the system 100 may further comprise other participant apparatuses 160, connected to the network 150 over connection 161, wherein tasks relating to the service system may be processed. The participant apparatus 160 may comprise the participant apparatus of a coordinator or administrator of the clinical trial, for example.

Different apparatuses 110, 120, 130, 160, 170 may provide clinical trial related information to be maintained in the service system 100. The information may be maintained as a collaborative clinical trial record 132 within the server apparatus 130, 131. The collaborative record 132 may comprise any trial related information provided by different participants, the service system or sensors, for example.

Furthermore, the coordinator of an apparatus 160 may define trial targets and recommendations. The system service 130, 131 may receive participant data and an event log relating to clinical trial generated by an electronic diary 124 of a client device 120 as input and process the received data and generate correction to timestamps of the event log corresponding to event entries of the electronic diary of the participant of the clinical trial.

In an embodiment, a server apparatus 130 maintains, by a service provider such as a sponsor or organizer of the clinical trial, the service system data, such as clinical trial related records. Each record may be identified using a participant identifier. The participant identifier may comprise, for example a unique number, string or an e-mail address, for example. In general, participant identifier must be unique but not something based on which someone can recognize or identify the user.

Information relating to clinical trial records, or event logs corresponding to event entries of an electronic diary, or any other participant related data, may be transmitted to the server 130 from a plurality of apparatuses 110, 120, 160 over the network 150. Eventually, the received service data is maintained, by an operator, at the server 130 comprising storage device 131, wherein the data being available for participants having access to that particular record. Furthermore, metadata associated with the service data may also be stored in the server 130 or storage device 131, such as location information, time information, or a device identifier, for example.

In an embodiment, clinical trial related data generated by a participant may travel to a server apparatus 130 over different paths. A first path may comprise sending data captured by a proprietary application (e.g. a clinical trial client application) of a client device 120 over a wireless communication network 122, 140, 141 and public data communication network 150, 151 to the server apparatus 130. A second path may comprise sending data captured by a default application (e.g. a browser) of a client device 120 over a wireless communication network 122, 140, 141 and public data communication network 150, 151 to the server apparatus 130. A third path may comprise sending data captured by a personal device 110 (such as user wearable sensor) to the client device 120 over connection 112 and therefrom over a wireless communication network 122, 140, 141 and public data communication network 150, 151 to the server apparatus 130. A fourth path may comprise sending data captured by the device 110 to a computer apparatus 120 and therefrom over the connection 123 and the public data communication network 150, 151 to the server apparatus 130.

In an embodiment, the proprietary application in the client device 120 may be a client application of a service whose server application is running on the server apparatus 130 of the system 100. The proprietary application may capture the data for the first path. Also metadata for the captured multimedia may be retrieved by the proprietary application from the metadata elements 121 of the client device 120. For the second path, the data captured by the default application may be imported to the proprietary application before transmitting to the server apparatus 130. The proprietary application may check the data and extract and apply metadata for the data. For the third path, the data may be captured by the external device 110 and transmitted to the proprietary application of the client device 120 for sending to the server apparatus 130. The proprietary application may check the data and extract and apply metadata for the multimedia data. A participant may provide additional metadata using the client device 120. For the fourth path, the data may be captured by the external device 110 and transmitted to a communication application of a computer apparatus 120. The communication application may check the multimedia data and extract and apply metadata for the multimedia data. The participant may provide additional metadata using the computer apparatus. In a further embodiment, the participant may access the data on the server apparatus and provide additional metadata.

In an embodiment, a proprietary or client application in the user apparatus 160 (e.g. administrator apparatus) may be an administrator application of a service whose server application is running on the server apparatus 130 of the system 100.

In an embodiment, the personal device 110 may comprise a user wearable device communicating with the apparatus 120 over a local connection 112. The local connection 112 may comprise, for example, at least one of the Bluetooth, Radio Frequency Identification (RF-ID), near field communication (NFC) or other wireless non-cellular connection. The wireless non-cellular connection may comprise industrial, scientific and medical (ISM) radio bands that are radio bands (portions of the radio spectrum) reserved internationally for the use of radio frequency (RF) energy for industrial, scientific and medical purposes, for example. Alternatively, the user wearable device 110 may be comprised by the apparatus 120, as illustrated by an integrated apparatus 121. The apparatus 110, 120 may be for example a wrist wearable user apparatus. Furthermore, the personal device 110 may be connected to the network 150 over local connection 113 corresponding to connection 123, for example.

In an embodiment, a communication interface module of the device 120 may comprise location modules for tracking location of the portable apparatus 120. Such location modules may comprise a module for providing a connection to satellite based global positioning system (e.g. GPS, not shown), a module for cellular based positioning system, a module for wireless non-cellular positioning system (e.g. Wi-Fi) or a module for hybrid positioning system, for example. The positioning system may also be used for user speed detection, altitude detection, route detection and route planning for various embodiments.

In an embodiment, the device 120 may be connected over a wireless or wired connection to a wide area network 150, such as Internet. Router apparatuses (not shown) may be used for providing the access to a wide area network 150. The access may comprise cellular or non-cellular connection.

In an embodiment, a proprietary application in the device 120 may be a client application of a service whose server application is running on the server apparatus 130 of the system 100. The proprietary application may capture the user input data for the service and provide the user output data from the service.

The server 130 may also provide a cloud service for the portable device 120 data. Optionally, further apparatuses may be added, such as peripheral devices for maintaining, providing or processing the portable device 120 data and communication devices for connecting the peripheral devices to the system 100.

In an embodiment, the system 100 may further comprise an external database 170. The external database 170 may be accessible to the network 150 over connection 171. The database 170 may have corresponding structure as the server apparatus 130, 131, for example.

Especially when using "Bring Your Own Device" (BYOD) terminals in a clinical trial, some problems arise.

For example, the system server 130, 131 does not know which applications control participant's device 120 clock because either native or third party application(s) may be in control.

The system server 130, 131 does neither know how network is setting a local time and what might be impacting on time setting for timestamp.

Within clinical trials, all client devices 120 are not run in online kiosk mode with trusted clock information all the time. The kiosk mode may comprise, for example, a kiosk application run in a client device 120 providing a mechanism for a yes/no prompt on a kiosk application screen online. Another mechanism is inputting consent form at the kiosk application screen online, letting the participant sign it and feed it back into the kiosk mode, e.g. within the electronic diary. Regardless of the method of signing, the consent obtained is digitally stored in the consent database and the consent event is recorded in the system. Participating users have interests to "backfill" data, known as "parking lot syndrome in clinical trials"). Thus, participants may retrospectively complete days or weeks of diaries just prior to submitting diaries, "in a parking lot". Furthermore, with an electronic device, participant may set back device time/date, enter data for a missed day, correct time/data to next missed day, repeat the procedure for each missed day (and may forget to set the time back to correct one while still using the clinical trial application for new entries). In both cases, the participant's motivation relates to remaining compliant, since else he/she faces chance to be dropped out of the clinical trial.

Online web diary doesn't have these problems—however, clinical trials prefer offline diaries. Main reason is that due to site locations of the clinical trial, participant may not be able attend sessions, un-treated participants are hard to find for the trial, and sponsors or clinical trial service providers do not want to prevent the participant from "going fishing" or flight mode during trial.

DCF (Data Clarification Form) process is a highly regulated process. The system records a Data Clarification Form (also known as Data Change Request or DCR), which are then automatically forwarded to the appropriate party for approval. No participant entered data can be amended without proper authorization: Data changes are via the authority of the investigator(s) and permission of the Sponsor. Individual privacy is governed in the US by Health Insurance Portability and Accountability Act (HIPAA) and in the EU by EU Directive 95/46/EEC ("Data Protection Directive"). Also other regulations, such as national Good Clinical Practice guidelines may govern data record editing processes in clinical trials. DCF (Data Clarification Form) as a highly regulated process is one reason why manual correction by a service provider of the clinical trial and setting the correct timestamp is painful, slow and complicated. By doing it according to embodiments disclosed, it is possible to reduce the manual administration required for the clinical trial.

Figure 2:
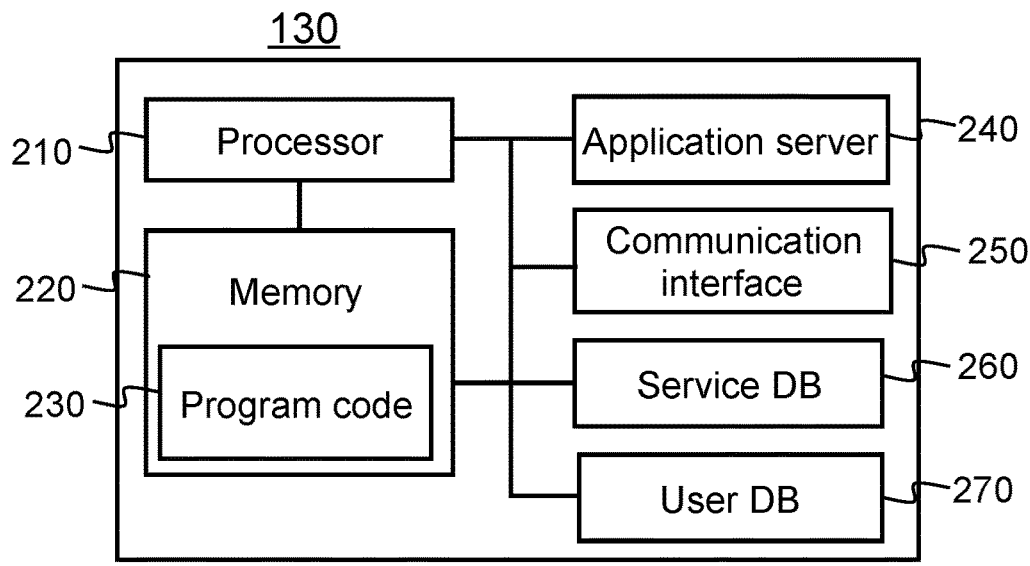
FIG. 2 shows a block diagram of the server apparatus of an example embodiment.

FIG. 2 presents an example block diagram of a server apparatus 130 in which various embodiments of the invention may be applied. All elements described in FIG. 2 are not necessary to be implemented in the same apparatus 130.

The general structure of the server apparatus 130 comprises a processor 210, and a memory 220 coupled to the processor 210. The server apparatus 130 further comprises software 230 stored in the memory 220 and operable to be loaded into and executed in the processor 210. The software 230 may comprise one or more software modules and can be in the form of a computer program product.

The processor 210 may be, e.g., a central processing unit (CPU), a microprocessor, a digital signal processor (DSP), a graphics processing unit, or the like. FIG. 2 shows one processor 210, but the server apparatus 130 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 220 may be constructed as a part of the server apparatus 130 or it may be inserted into a slot, port, or the like of the server apparatus 130 by a participant. The memory 220 may serve the sole purpose of storing data, or it may be constructed as a part of an apparatus serving other purposes, such as processing data.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), GSM/GPRS, CDMA, WCDMA, or LTE (Long Term Evolution) radio module. The wired interface may comprise such as Ethernet or universal serial bus (USB), for example. The communication interface module 250 may be integrated into the server apparatus 130, or into an adapter, card or the like that may be inserted into a suitable slot or port of the server apparatus 130. The communication interface module 250 may support one radio interface technology or a plurality of technologies. Configuration information between the client device 120 and the system server 130 may be transceived using the communication interface 250. Similarly, account creation information between the system server 130 and a service provider may be transceived using the communication interface 250.

An application server 240 provides application services e.g. relating to the participant accounts stored in a participant database 270 and to the service information stored in a service database 260. Different application services may be provided to different users, such as the first user (client participating the clinical trial), the second user (coordinator/administrator of the trial) and the third user (sponsor of the trial).

A skilled person appreciates that in addition to the elements shown in FIG. 2, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. In an embodiment, the server apparatus 130 may receive an event log corresponding to event entries of an electronic diary of a participant of a clinical trial, wherein the electronic diary and the event log are generated in a client device, and the event log comprising an event identifier and an event timestamp for each event entry; determine a block of event entries within the event log, the block comprising a first event entry and a second event entry at least one of whose event timestamps are verified being correct in view of corresponding service timestamps of a server apparatus, wherein the second event entry having a later event timestamp than the first event entry; detect a third event entry whose event timestamp is temporally between the first and second timestamps; adjust automatically the event timestamp of the third event entry based on at least one of the first and the second timestamps; and generate a tag to the third event entry for indicating automatic adjusting of the event timestamp.

Furthermore, the server apparatus 130 may be configured to determine a time correction for the event timestamp of the second event; adjust the event timestamp of the second event entry based on the time correction; and adjust the event timestamp of the third event entry based on the time correction.

Furthermore, the server apparatus 130 may be configured to determine a minimum time value for the event timestamp of the third event based on the event timestamp of the of the third event and a timestamp of at least one previous event; determine a maximum time value for the event timestamp of the third event based on the event timestamp of the of the third event and a timestamp of at least one following event; define a time range using the minimum time value and the maximum time value; and adjust the event timestamp of the third event entry based on the time range.

Furthermore, the server apparatus 130 may be configured to approve the third event entry as valid entry for trial data of the clinical trial in response to generation of the tag indicating automatic adjusting of the event timestamp.

Furthermore, the server apparatus 130 may be configured to synchronize the local clock information of the client device using the trusted clock information of the server apparatus. The trusted clock information of the server apparatus may also comprise clock information fetched from a trusted source over the network 150.

Figure 3:
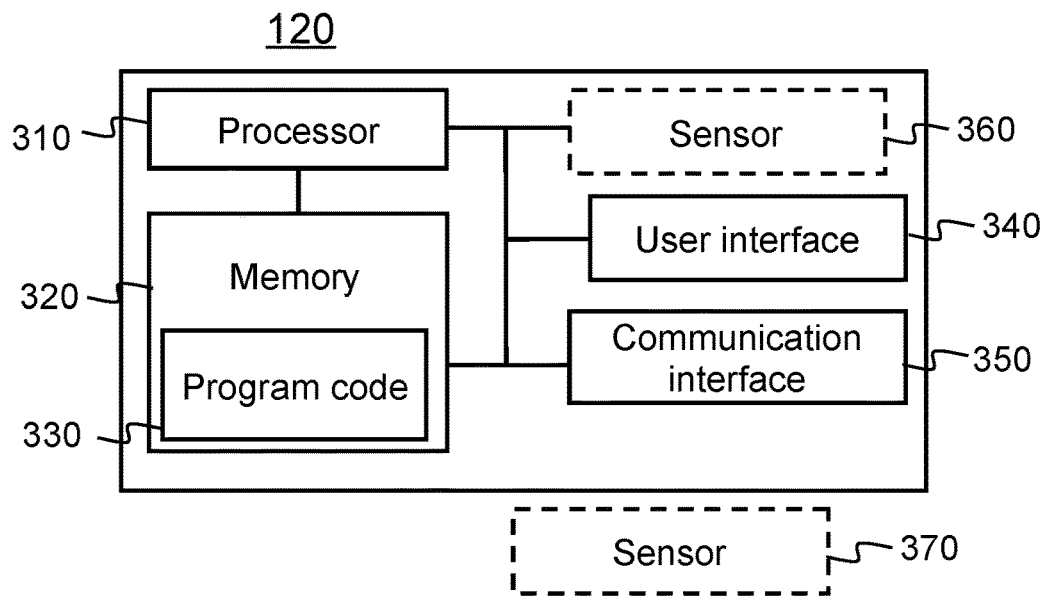
FIG. 3 shows a block diagram of a client device of an example embodiment.

FIG. 3 shows a block diagram of a client device of an example embodiment. In an embodiment, a sensor 360, 370 may be implemented as a separate device 370 communicating via the communication interface 350 with the client device 120, or as an integrated sensor 360 within the device 120. The user interface 340 may be implemented also in another device connected via a communication interface 350 to the device 120. Such device may comprise a mobile phone, a smart phone, or a tablet, for example. In an embodiment, the device 120 may communicate with a plurality of sensors 360, 370, both internal and external sensors, and of a plurality of participants. In an embodiment, the sensor 360 may also comprise a camera for capturing multimedia data to be submitted to the server apparatus 130, 131 as participant data, event data for the clinical trial, for determination of preliminary trauma information or for creating multimedia data, for example.

The general structure of the device 120 comprises a user interface 340, a communication interface 350, a processor 310, and a memory 320 coupled to the processor 310. The device 120 further comprises software 330 stored in the memory 320 and operable to be loaded into and executed in the processor 310. The software 330 may comprise one or more software modules and can be in the form of a computer program product. Not all elements of FIG. 3 are necessary but optional for the portable apparatus 120, such as the sensor 360, 370.

In an embodiment, an electronic diary is a computer-implemented client software application 330 for a participant of a clinical trial to record data for the clinical trial. The electronic diary may also comprise a computer-implemented web browser application. The electronic diary may also comprise a combination of a client software application and a browser application.

The processor 310 may be, e.g., a central processing unit (CPU), a microprocessor, a digital signal processor (DSP), a graphics processing unit, or the like. FIG. 3 shows one processor 310, but the device 120 may comprise a plurality of processors.

The memory 320 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The device 120 may comprise a plurality of memories. The memory 320 may be constructed as a part of the device 120 or it may be inserted into a slot, port, or the like of the device 120 by a user. The memory 320 may serve the sole purpose of storing data, or it may be constructed as a part of an apparatus serving other purposes, such as processing data.

The user interface 340 may comprise circuitry for receiving input from a user of the device 120, e.g., via a keyboard, a touchpad, a motion sensor, a touchscreen of the device 120, speech recognition circuitry, gesture recognition circuitry or an accessory device, such as a headset or a remote controller, for example. Furthermore, the user interface 340 may comprise circuitry for providing output for the user via a display, a speaker, a touch-sensitive display or a tactile feedback device, for example.

In an embodiment, a user may speak during the clinical trial when generating electronic diary relating to sensations during the trial and the speech is automatically converted to feedback information for the system. Thus feedback is always up-to-date and accurate.

The communication interface module 350 implements at least part of data transmission. The communication interface module 350 may comprise, e.g., a wireless or a wired interface module. The wireless interface may comprise such as a WLAN, Bluetooth, infrared (IR), radio frequency identification (RF ID), NFC, GSM/GPRS, CDMA, WCDMA, or LTE (Long Term Evolution) radio module. The wired interface may comprise such as universal serial bus (USB), HDMI, SCART or RCA, for example. The communication interface module 350 may be integrated into the device 120, or into an adapter, card or the like that may be inserted into a suitable slot or port of the device 120. The communication interface module 350 may support one radio interface technology or a plurality of technologies. The communication interface module 350 may support one wired interface technology or a plurality of technologies. The device 120 may comprise a plurality of communication interface modules 350.

In an embodiment, the communication interface module 350 may comprise location modules for tracking location of the device 120. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 350 with a satellite based global positioning system (e.g. GPS) may detect altitude of the participant to provide an estimate of thinness of air. Such estimate of air thinness may be used as input for determining characteristics of the event for the electronic diary.

A skilled person appreciates that in addition to the elements shown in FIG. 3, the device 120 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the device 120 may comprise a disposable or rechargeable battery (not shown) for powering when external power supply is not available.

In an embodiment, the device 120 comprises speech or gesture recognition means. Using these means, a pre-defined phrase or a gesture may be recognized from the speech or the gesture and translated into control information for the device 120.

Figure 4:
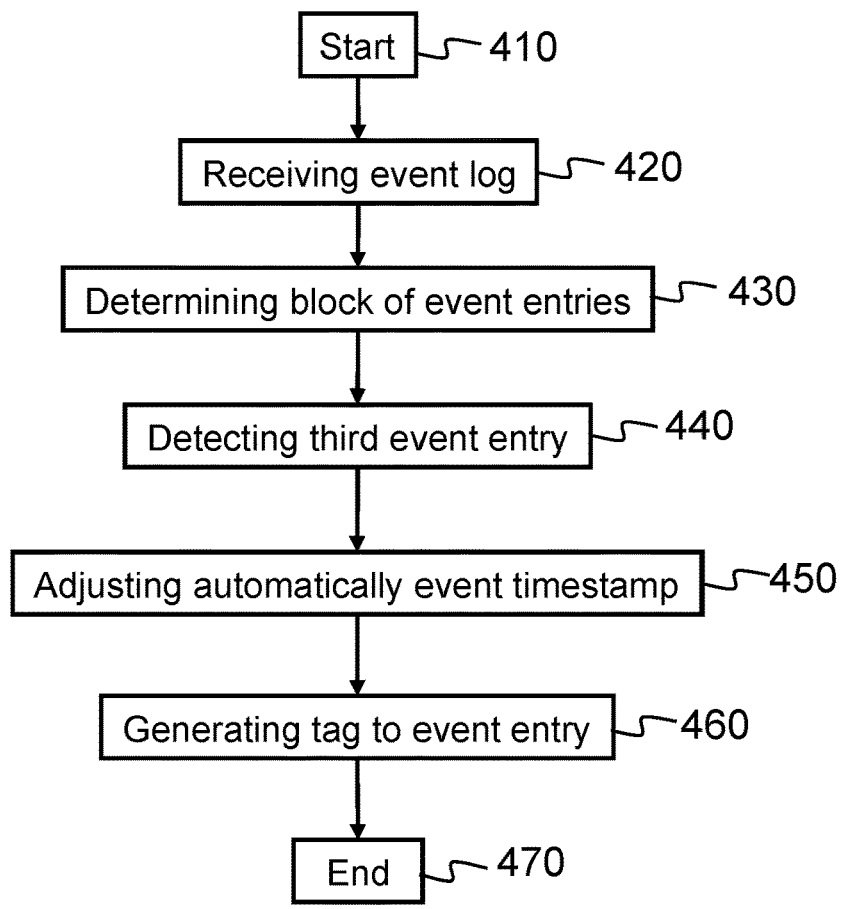
FIG. 4 shows a flow chart of a process of an example embodiment.

FIG. 4 shows a flow chart of a process according to an example embodiment of the invention.

A method starts in step 410. In step 420, an event log is received corresponding to event entries of an electronic diary of a participant of a clinical trial, wherein the event log is generated in a client device, and the event log comprising an event identifier and an event timestamp for at least two event entries. In step 430, a block of event entries is determined within the event log, the block comprising a first event entry and a second event entry at least one of whose event timestamps are verified being correct in view of corresponding service timestamps of a server apparatus, wherein the first and the second event entry are arranged chronologically. In step 440, a third event entry may be detected (not necessarily), whose event timestamp is temporally between the first and second timestamps. In step 450, the event timestamp of the second or third event entry is adjusted based on the first timestamp or at least one of the first and the second timestamps, respectively. In step 460, a tag is generated (not necessarily) to the second or the third event entry for indicating adjusting of the event timestamp. In step 470, the method ends.

When thinking about clinical trials and collecting clinical trial data from remote participants, one basic problem with devices other than those run in kiosk mode is that the administrator/coordinator/service system provider receiving the data has no control over the time and date settings of the remote device. This is especially true with "Bring Your Own Device" (BYOD) terminals in a clinical trial. The system server cannot force the client device to connect to a network nor can it force the remote device to get the time and date from the network prior to usage.

When devices are run on kiosk mode, the server updates the remote device's time and date so the system server is in control, at least at times the remote device is connected to the server.

Figure 5:
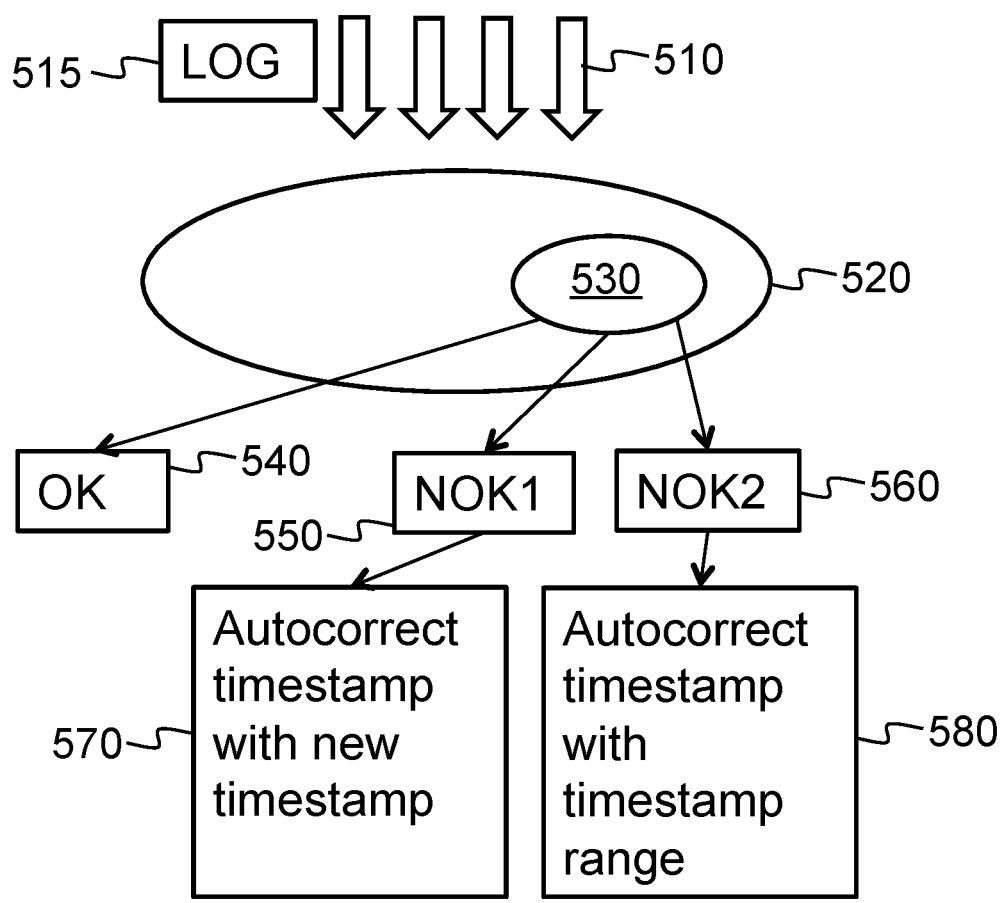
FIG. 5 shows a schematic drawing of analysis and correction process of collector entries of an example embodiment.

FIG. 5 shows a schematic drawing of analysis and correction process of collector entries of an example embodiment.

Participants of a clinical trial may send electronic diary of events 510 and an event log 515 corresponding to the event entries with timestamps. The chronological order of the events and the client device clock time of the events (this can be called as event log) is known when received by the system server 520 and processed and analysed by an algorithm 530 of the server 520. The event log 515 contains, for example:

Events when the system server 520 knows the exact time (events when the time is synched with trusted clock)

Events when the time can change in uncontrolled manner (e.g. participant exits the client application)

Events when the client time is controlled again (e.g. participant enters to client application)

Events (Transactions) which time the system server 520 wants to check (if the client time is ok and if not, what is the correct time) (For example: Questionnaire filled)

In an embodiment, each event 510 contains identifier that can be used to bind the event to the created/updated entity on the server side 520. The event log 515 is sent to the server 520 together with actual changes and then analysed on server side 520, 530. Events 510 may correspond to participant data send to the server apparatus.

When analysing the events 510, by an algorithm 530 run by the server 520, the event log 515 may be divided to blocks that start and end with an event the time of which at least one is known to be correct. That block can then be analysed in more detail. From the block start all event times are ok for sure until the first event where the time can change. If the block ends to the event where the time was confirmed to be ok, then all the event times are ok for sure until the first event where the time can change. Such events are labelled OK and approved as valid events 540 for the clinical trial.

If the block ends to the event 510 where the time was corrected, then all the event times from the end until the first event where the time can change can be calculated based on time correction. Such events 550 are labelled NOK1 and approved as valid events 570 for the clinical trial, wherein the timestamp of the event entry is automatically corrected with an adjusted timestamp.

If there is more than just one event 510 where the time can change, between those events 510, the exact time cannot be calculated anymore, but time range can still be calculated. For example, a minimum time is calculated from the block start time (+ time passed when the application has been controlling the clock changes) and a maximum time is calculated from the block end time (− time passed when the application has been controlling the clock changes). Such events 560 are labelled NOK2 and approved as valid events 580 for the clinical trial, wherein the timestamp of the event entry is automatically corrected with a timestamp range.

After block is analysed, the analysis result can be bind to the entities on server side (For example: create DCF (Data Clarification Form) for the questionnaire whose filling time is analysed to be incorrect).

In an embodiment, the time of a local clock within the client device is synched with the trusted clock of the server.

Figure 6:
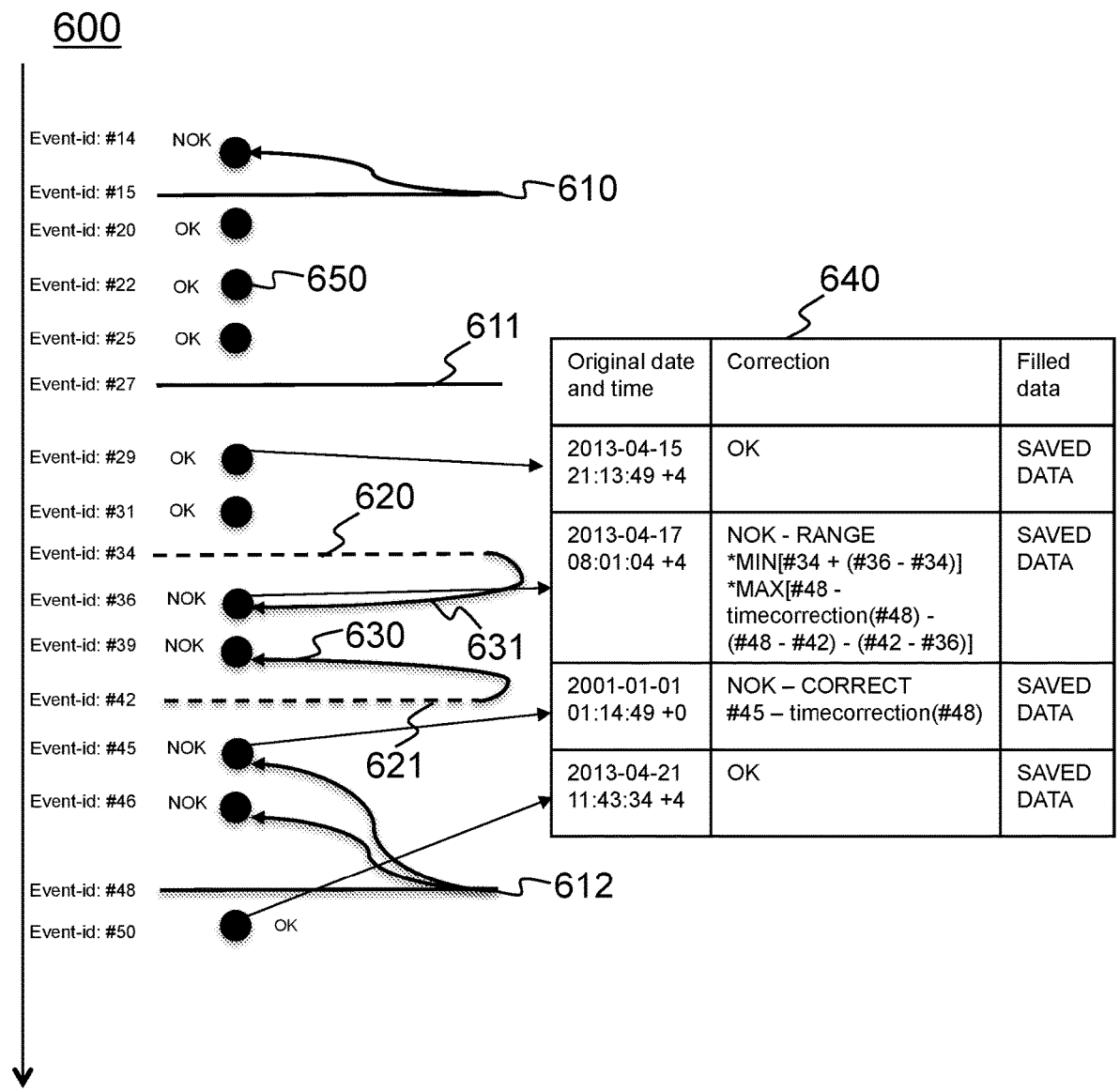
FIG. 6 shows a schematic illustration of event log and timestamp correction according to an embodiment.

FIG. 6 shows a schematic illustration of event log and timestamp correction according to an embodiment.

FIG. 6 shows an event log 600 of form-filling events and data in database that can be mapped with any unique identifier according to another example embodiment of the invention. The unique identifier may comprise device data and time stamp or unique event hash, for example.

A plurality of events 650 are shown in chronological order, wherein each event is identified using an event identifier, e.g. #14. Not all events are shown in FIG. 6 for clarity reasons but only events that effect analysis are shown.

Events 610-612 illustrated as solid lines correspond to events when clock is known to be correct. Such event may comprise, for example, kiosk mode event, event during online connection and clock synchronization, for example.

Events 620-621 illustrated as dashed lines correspond to events when clock is not known to be correct but regarded as suspicious. Such event may comprise, for example, event made after reboot of the client device, automatic event made by the client device with unsure time, event after non-active time period exceeding threshold value, event after software update of the client device, or event after change of geographical location, for example.

Event (id: #14) 610 illustrates the first event when clock of the client device is known to be correct. Events of the event log 600 following the event 610 are analysed to be OK in view of their timestamps until the next suspicious event (id: #34) 620. Then again following events #36-#46 are tagged as NOK (Not OK) and timestamps of such events are analysed and adjusted accordingly.

In an embodiment, when analysing the event log 600 received from the client device, a minimum time value 631 of the event #36 timestamp is determined based on the event timestamp of the of the event #36 (as received) and a timestamp of at least one previous event, e.g. event #34, as shown in FIG. 6. Table 640 shows some illustrative details of original timestamp, timestamp correction and filled entry data. Furthermore, a maximum time value 630 of the event #36 timestamp is determined based on the event timestamp of the event #36 (as received) and a timestamp of at least one following event, e.g. events #42 and #48, as shown in FIG. 6 and in table 640. Thus, a time range may be defined using the minimum time value (MIN) and the maximum (MAX) time value, wherein MIN value may be defined as:

[#34+(#36−#34)]

and MAX value may be defined as:

[#48−timecorrection(#48)−(#48−#42)−(#42−#36)], as illustrated in table 640.

In an embodiment, the event timestamp of the event #36 entry may be adjusted based on the time range defined.

In an embodiment, the event timestamp of the event #36 may be adjusted by adding the time range as the event time stamp of the event #36.

In an embodiment, the event timestamp of the event #36 may be adjusted manually by a coordinator or an administrator of the clinical trial by selecting a time value from the time range defined.

In an embodiment, the event timestamp of the event #36 may be adjusted by the server apparatus based on the time range defined. For example, the computer-implemented software algorithm at the server apparatus may generate the event time stamp by calculating a mean value within the time range based on the time range defined. Statistical analysis data and/or history data may also be used as an input for the algorithm, in addition to the time range defined, to adjust the event time stamp within the time range defined.

Thus, the timestamp can be ranged between event when clock turned suspicious—and between the last "trusted" event, enabling forecasted accuracy.

In an embodiment, event #45 timestamp is tagged as NOK (Not OK) and further analysis for timestamp correction is needed. Timestamp of the event #45 is corrected based on the original timestamp of the event #45 and the next reliable event's #48 timestamp, as shown in FIG. 6 and table 640.

Event #48 illustrates a trusted event with reliable timestamp. Thus, timestamp data of previous NOK event #45, #46 can be corrected based on time between trusted event #48 and data filling event #45, #46.

In an embodiment, a computer implemented method comprises:

receiving an event log corresponding to event entries of an electronic diary of a participant of a clinical trial, wherein the event log is generated in a client device, and the event log comprising at least two event entries, each of the at least two event entries associated with an event identifier and an event timestamp;

determining a block of event entries within the event log, the block comprising a first event entry and a second event entry at least one of whose event timestamps are verified being correct in view of corresponding service timestamps of a server apparatus, wherein the first and the second event entry are arranged chronologically; and adjusting the event timestamp of at least one of the first and the second event entry based on the timestamp verified being correct.

In an embodiment, the event timestamp of the second event entry is adjusted based on the event timestamp of the first event entry.

In an embodiment, a terminal log 515, 600 may contain all relevant events 510, 610-612, 620-621, 650 with a timestamp when the event 510, 650 took place in a diary 124 such as when forms were saved and data sent.

Every time data is sent, a device 110, 120 clock is synchronized with a server 130 time. If the device 110, 120 time was incorrect, the time is updated based on the server 130 time after the data is sent.

When a device 110, 120 is powered off, the time of the device 110, 120 may be lost due to a drained battery, for example. Reference can be made to the device 110, 120 being powered off and powered on as a "Restart". If the device 110, 120 lost the time while it was powered off, events (e.g. forms) saved after the restart until the next data-sending event will end up having incorrect timestamps.

From a data-sending event, the time difference to the server 130 time is known, such as how much "off" the device 110, 120 time was in comparison to the server 130 time. The algorithm of the computer-implemented method may use this time difference to calculate what was the correct time of the forms that were saved prior to the data-sending event. Sometimes the device 110, 120 may be restarted several times between two data-sending events. It may be impossible to conclude exclusively what was the correct time for forms that were saved between two such "Restart" events. For such forms, it may be possible to propose a possible time range during which the form was saved. The start and end points of this time range (min and max range value) are the points in time in the log file when it was certain that time was confirmed to be correct. The algorithm may not trust manual time adjustments done by the end user. A manual time adjustment may be treated like a "Restart" as there is no way to ensure that the end user corrected time manually correctly.

In an embodiment, correctness/incorrectness information of an event (e.g. a form marked as NOK) may be determined.

In a first scenario, event (e.g. a form) save time is outside a range. In this case it is certain that the event (e.g. a form) has incorrect save time as it is known that the event (e.g. a form) was saved during the range, and the time of the event (e.g. a form) is not inside that range. For example, the range is 04-Apr-2017 12:04:00-12-Apr-2017 16:32:00, but an event (e.g. a form) save time is 01-Jan.-1980 13.44:02. However, because of the multiple restarts of the device 110, 120 between two data-sending events, it is impossible to state what is the correct time of the event (e.g. a form). All we can know is that the event (e.g. a form) with timestamp 01-Jan.-1980 13.44:02 was saved at some point in time between 04-Apr-2017 12:04:00 and 12-Apr-2017 16:32:00.

In a first scenario, an event (e.g. a form) save time is inside a range. In this case it is unclear whether the event (e.g. a form) has correct/incorrect save time. For example, the range is 04-Apr-2017 12:04:00-12-Apr-2017 16:32:00 and event (e.g. a form) save time is 04-Apr-2017 17:54:00. It could be that the event (e.g. a form) save time is correct or that the event (e.g. a form) save time is incorrect, however it is difficult to get any more specific information than that the event (e.g. a form) was saved in the range.

In an embodiment, tolerance based filtering may be utilized. Such filtering is a way to filter out timestamps that have acceptable time shifts i.e. the algorithm can tolerate such time shifts. For example, the algorithm script is configured to run with a default tolerance of 1 h. This means that the algorithm accepts that an event (e.g. a form) had incorrect time of +/−1 h. In the report, a tolerance filter can be further applied that extends the tolerance window further, for example to 4 h or 24 h.

Events (e.g. forms) that have a save time within the time window of an exact time suggestion +/− the tolerance will be excluded from the result—the algorithm may thus consider this time difference to be acceptable.

Event (e.g. a form) save time from the log file may fall inside a range. An event (e.g. a form) will be excluded from the results if the difference between suggested max and min values is smaller than the tolerance. For example, suggested range is 12:00-15:00 (3 h). Event (e.g. a form) save time in terminal log can be anything between this time range. When the algorithm applies a tolerance of 4 h, the event (e.g. a form) may be excluded from the results. When applying a tolerance of 1 h, the event (e.g. a form) may be included in the results.

If the event (e.g. a form) save time falls outside the range, the event (e.g. a form) is included. If there is a range defined with missing min value, then the tolerance filter is not applied to such event (e.g. a form).

In an embodiment, no minimum range is defined. Such scenario is similar to the other scenario, where the event (e.g. a form) was saved between two restart events and no data-sending took place between these restart events. What makes this scenario more problematic is that the first one of these restart events was the first time ever that the device 110, 120 was powered on. Now the algorithm has no known time reference confirmed in the log file prior to this first "power on" event that can be used as confirmed known time for the minimum range.

Thus, to determine whether a timestamp was incorrect or not, manual analysis may be done. The minimum range may be confirmed from other resources. Undoubtedly the event (e.g. a form) was created after the subject joined the study or the study started, so if the event (e.g. a form) save time is very much in the past e.g. year is 1980, then it can be determined that the timestamp was most certainly incorrect. If event (e.g. a form) save time is close to the max range value, it is likely that the event (e.g. a form) has correct save time, but this cannot be known for certain. All that is known for sure is that the event (e.g. a form) was saved after subject started the study but before the suggested max range.

Without in any way limiting the scope, interpretation, or application of the claims appearing below, a technical effect of one or more of the example embodiments disclosed herein is improved method and apparatus for providing clinical trial related information. Another technical effect of one or more of the example embodiments disclosed herein is cleaner data with auto-correct implementation. Another technical effect of one or more of the example embodiments disclosed herein is that manual work is reduced. Another technical effect of one or more of the example embodiments disclosed herein is that timestamps of clinical trial events are more accurate. Another technical effect of one or more of the example embodiments disclosed herein is that only a single system is need and no complex dedicated client devices are needed, and a wide variety of mobile devices, smartphones, tablets and computers may be used to provide more simple system.

In an embodiment, each participant may be identified by a participant identifier that may be verified when a participant profile is created to the system. Each participant may be defined access rights within the system for certain parts of the information within the clinical trial records.

If desired, the different functions discussed herein may be performed in a different order and/or concurrently with each other. Furthermore, if desired, one or more of the before-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications, which may be made without departing from the scope of the present invention as defined in the appended claims.

However, claimed embodiments do not constitute a method step for treatment of the human or animal body by surgery or therapy. No functional relationship exists between the steps related to apparatus and any therapeutic effect of the apparatus on the body.

The invention claimed is:

1. A computer implemented method comprising:
    receiving an event log corresponding to event entries of an electronic diary of a participant of a clinical trial, wherein the event log is generated in a client device, and the event log comprising at least two event entries, each of the at least two event entries associated with an event identifier and an event timestamp;
    determining a block of event entries within the event log, the block comprising a first event entry and a second event entry at least one of whose event timestamps are verified being correct in view of corresponding service timestamps of a server apparatus, the server apparatus comprising a storage device for storing the event log, wherein the first and the second event entry are arranged chronologically;
    maintaining trusted clock information at the server apparatus for providing service timestamps used for verification of event timestamps of the at least two event entries;
    generating a tag to at least one event entry for indicating the automatic adjusting of the event timestamp;
    approving the event entry as valid entry for trial data of the clinical trial in response to generation of the tag indicating the automatic adjusting of the event timestamp;
    adjusting the event timestamp of at least one of the first and the second event entry based on the timestamp verified being correct;
    generating a synchronization message for the client device in response to adjusting the event timestamp;
    executing a synchronization when the client device and the server apparatus are connected to each other for data transfer;
    modifying a local clock of the client device based on a time correction value in the synchronization message;
    receiving participant data from the client device or a personal device;
    maintaining the event log and the participant data generated by the electronic diary at the server apparatus for clinical trial processing, wherein the participant data being recorded by the personal device without user input.

2. The method of claim 1, further comprising:
    receiving the event log corresponding to event entries of an electronic diary of a participant of a clinical trial, wherein the event log is generated in a client device, and the event log comprising an event identifier and an event timestamp for at least three event entries;
    determining a block of event entries within the event log, the block comprising a first event entry and a second event entry at least one of whose event timestamps are verified being correct in view of corresponding service timestamps of a server apparatus, wherein the second event entry having a later event timestamp than the first event entry;
detecting a third event entry whose event timestamp is temporally between the first and second timestamps; and
adjusting the event timestamp of the third event entry based on at least one of the first and the second timestamps.

3. The method of claim 1, further comprising:
maintaining the local clock information at the client device for providing event timestamps for the event entries.

4. The method of claim 1, wherein at least one of the electronic diary and the event log is associated with a participant identifier or a client device identifier of the participant of the clinical trial.

5. The method of claim 2, further comprising:
determining a time correction for the event timestamp of the second event; and
adjusting the event timestamp of the second event entry based on the time correction; and
adjusting the event timestamp of the third event entry based on the time correction.

6. The method of claim 2, further comprising:
determining a minimum time value for the event timestamp of the third event based on the event timestamp of the third event and a timestamp of at least one previous event;
determining a maximum time value for the event timestamp of the third event based on the event timestamp of the third event and a timestamp of at least one following event;
defining a time range using the minimum time value and the maximum time value; and
adjusting the event timestamp of the third event entry based on the time range.

7. The method of claim 3, further comprising:
synchronizing the local clock information of the client device using the trusted clock information of the server apparatus.

8. The method of claim 7, wherein the synchronization is done when the client device and the server apparatus are connected to each other for data transfer.

9. The method of claim 1, further comprising:
receiving the event log from the client device; and
maintaining the event log generated by the electronic diary at the server apparatus for clinical trial processing.

10. The method of claim 1, wherein the personal device comprising a user wearable device.

11. The method of claim 1, wherein the participant data being recorded by the electronic diary before sending to the server apparatus.

12. The method of claim 1, further comprising retrieving trial data of an on-going clinical trial from trial records maintained at the server apparatus, wherein retrieving the trial data includes retrieving the trial data having a level of cleanliness satisfying a predetermined criterion of a cleanliness.

13. The method of claim 12, wherein the predetermined criterion of a cleanliness comprising at least one of the following:
a threshold value for an amount of event entries comprising a tag for indicating the adjusting of the event timestamp; and
a threshold value for a proportional share of event entries comprising a tag for indicating the adjusting of the event timestamp.

14. The method of claim 1, further comprising:
transmitting the synchronization message for the client device for synchronizing the local clock of the client device based on the time correction value.

15. A server apparatus comprising:
a communication interface for transmitting information over a network;
at least one memory including computer program code; the at least one memory and the computer program code configured to, with the at least one processor, cause the server apparatus to:
receive an event log corresponding to event entries of an electronic diary of a participant of a clinical trial, wherein the event log is generated in a client device, and the event log comprising at least two event entries, each of the at least two event entries associated with an event identifier and an event timestamp;
determine a block of event entries within the event log, the block comprising a first event entry and a second event entry at least one of whose event timestamps are verified being correct in view of corresponding service timestamps of a server apparatus, the server apparatus comprising a storage device for storing the event log, wherein the first and the second event entry are arranged chronologically;
maintaining trusted clock information at the server apparatus for providing service timestamps used for verification of event timestamps of the at least two event entries;
generating a tag to at least one event entry for indicating the adjusting of the event timestamp;
approving the event entry as valid entry for trial data of the clinical trial in response to generation of the tag indicating the adjusting of the event timestamp;
adjusting the event timestamp of at least one of the first and the second event entry based on the timestamp verified being correct;
generating a synchronization message for the client device in response to adjusting the event timestamp;
executing a synchronization when the client device and the server apparatus are connected to each other for data transfer;
modifying a local clock of the client device based on a time correction value in the synchronization message;
receiving participant data from the client device or a personal device;
maintaining the event log and the participant data generated by the electronic diary at the server apparatus for clinical trial processing, wherein the participant data being recorded by the personal device without user input.

16. A computer program embodied on a computer readable non-transitory medium comprising computer executable program code, which when executed by at least one processor of an apparatus, causes the apparatus to:
receive an event log corresponding to event entries of an electronic diary of a participant of a clinical trial, wherein the event log is generated in a client device, and the event log comprising at least two event entries, each of the at least two event entries associated with an event identifier and an event timestamp;
determine a block of event entries within the event log, the block comprising a first event entry and a second event entry at least one of whose event timestamps are verified being correct in view of corresponding service timestamps of a server apparatus, the server apparatus comprising a storage device for storing the event log, wherein the first and the second event entry are arranged chronologically;

maintaining trusted clock information at the server apparatus for providing service timestamps used for verification of event timestamps of the at least two event entries;

generating a tag to at least one event entry for indicating the adjusting of the event timestamp;

approving the event entry as valid entry for trial data of the clinical trial in response to generation of the tag indicating the adjusting of the event timestamp;

adjusting the event timestamp of at least one of the first and the second event entry based on the timestamp verified being correct;

generating a synchronization message for the client device in response to adjusting the event timestamp;

executing a synchronization when the client device and the server apparatus are connected to each other for data transfer;

modifying a local clock of the client device based on a time correction value in the synchronization message;

receiving participant data from the client device or a personal device;

maintaining the event log and the participant data generated by the electronic diary at the server apparatus for clinical trial processing, wherein the participant data being recorded by the personal device without user input.

* * * * *